United States Patent
Roodaki et al.

(10) Patent No.: US 11,944,571 B2
(45) Date of Patent: Apr. 2, 2024

(54) TREATMENT APPARATUS WITH AN OPTICAL COHERENCE TOMOGRAPHY DEVICE, AND METHOD FOR CORRECTING AN OCT CROSS-SECTIONAL IMAGE

(71) Applicant: CARL ZEISS MEDITEC AG, Jena (DE)

(72) Inventors: Hessam Roodaki, Oberkochen (DE); Mhd Hasan Sarhan, Oberkochen (DE); Abouzar Eslami, Oberkochen (DE)

(73) Assignee: CARL ZEISS MEDITEC AG, Jena (DE)

( * ) Notice: Subject to any disclaimer, the term of this patent is extended or adjusted under 35 U.S.C. 154(b) by 0 days.

(21) Appl. No.: 18/461,787

(22) Filed: Sep. 6, 2023

(65) Prior Publication Data

US 2024/0074896 A1 Mar. 7, 2024

(30) Foreign Application Priority Data

Sep. 6, 2022 (DE) ...................... 10 2022 122 511.9

(51) Int. Cl.
*A61F 9/007* (2006.01)
*A61B 3/10* (2006.01)
*A61F 2/16* (2006.01)
*A61B 34/10* (2016.01)

(52) U.S. Cl.
CPC .......... *A61F 9/00736* (2013.01); *A61B 3/102* (2013.01); *A61F 2/16* (2013.01); *A61B 2034/107* (2016.02); *A61F 2002/1681* (2013.01)

(58) Field of Classification Search
CPC ........ A61F 9/00736; A61F 2009/00851; A61F 2009/00882; A61F 2009/00887; A61F 2009/00897
See application file for complete search history.

(56) References Cited

U.S. PATENT DOCUMENTS 8,708,488 B2    4/2014   Kraus et al.

FOREIGN PATENT DOCUMENTS

DE    102008034490 A1    2/2010
DE    102016105962 A1    10/2017

OTHER PUBLICATIONS

English Translation of German Office Action for (DE 10 2022 122 511.9) dated Aug. 5, 2023 (6 pages).

*Primary Examiner* — William H Matthews
(74) *Attorney, Agent, or Firm* — ALSTON & BIRD LLP (57) ABSTRACT

The invention relates to a treatment apparatus having a modular intraocular lens, which comprises a first part having a haptic and a marking, visible in optical coherence tomography, with known dimensions of said marking and a second part having an optics body and which has a convergence state, in which the second part is in contact with the first part, and a spaced-apart state, in which the second part is spaced apart from the first part, having an optical coherence tomography device, which is configured to record, by means of optical coherence tomography, an OCT cross-sectional image which shows the first part arranged in a capsular bag of an eye and which shows dimensions of the marking in the OCT cross-sectional image, and having an evaluation unit which is configured to create a corrected OCT cross-sectional image by transforming coordinates of the OCT cross-sectional image in such a way that dimensions of the marking in the corrected OCT cross-sectional image are closer to the known dimensions of the marking than the dimensions of the marking in the OCT cross-sectional image.

10 Claims, 5 Drawing Sheets

TREATMENT APPARATUS WITH AN OPTICAL COHERENCE TOMOGRAPHY DEVICE, AND METHOD FOR CORRECTING AN OCT CROSS-SECTIONAL IMAGE

CROSS-REFERENCE TO RELATED APPLICATIONS

This application claims priority to German Patent Application No. 10 2022 122 511.9, filed Sep. 6, 2022, the entire contents of which are incorporated herein by reference.

The invention relates to a treatment apparatus for a cataract treatment of an eye, the treatment apparatus comprising an optical coherence tomography device, and to a method for correcting an OCT cross-sectional image.

Figure 6:
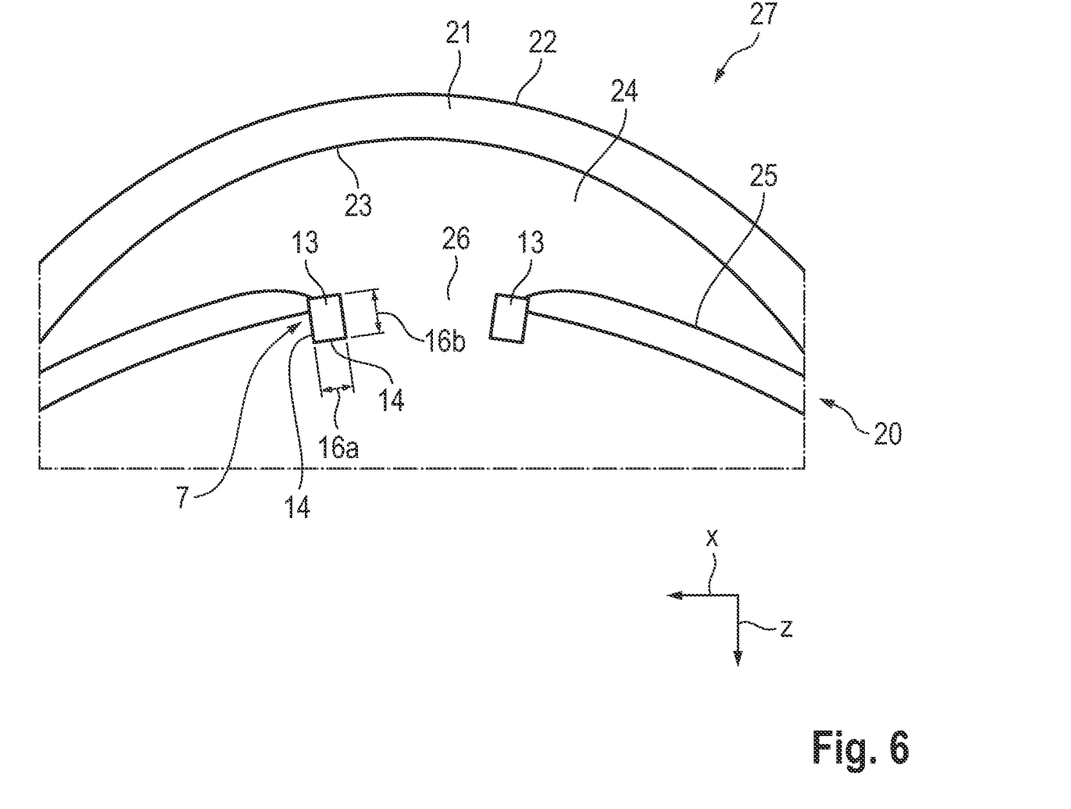
FIG. 6 shows an exemplary OCT cross-sectional image.

In a cataract treatment, a crystalline lens of an eye is replaced with an artificial intraocular lens. To this end, an incision with a length of approx. 2 mm is introduced into the eye. Via the incision, the crystalline lens is for example comminuted by means of phacoemulsification and subsequently aspirated. The intraocular lens is subsequently introduced into the eye via the incision. Prior to the cataract treatment, the eye can be measured, for example by means of optical coherence tomography (OCT), in order to determine the properties such as the refractive power of the intraocular lens to be inserted. Within the scope of optical coherence tomography, a beam of electromagnetic radiation, more particularly infrared radiation, can for example be steered along a line to different positions in the eye, thus carrying out what is known as a B-scan. Since optical coherence tomography provides information about the depth in the eye at which reflecting or scattering structures are arranged, an OCT cross-sectional image of the eye can be obtained by way of such a B-scan. FIG. 6 shows such an OCT cross-sectional image 20. The eye changes during the cataract treatment, especially as a result of the introduction of the incision into the eye and the aspiration of the crystalline lens. As a result, the OCT cross-sectional image recorded prior to the cataract treatment no longer corresponds to the actual conditions during the cataract treatment. This may lead to the insertion of an intraocular lens which does not have optimal properties for the eye. It would therefore be desirable to carry out optical coherence tomography after the crystalline lens has been removed but before the intraocular lens is inserted.

Figure 1:
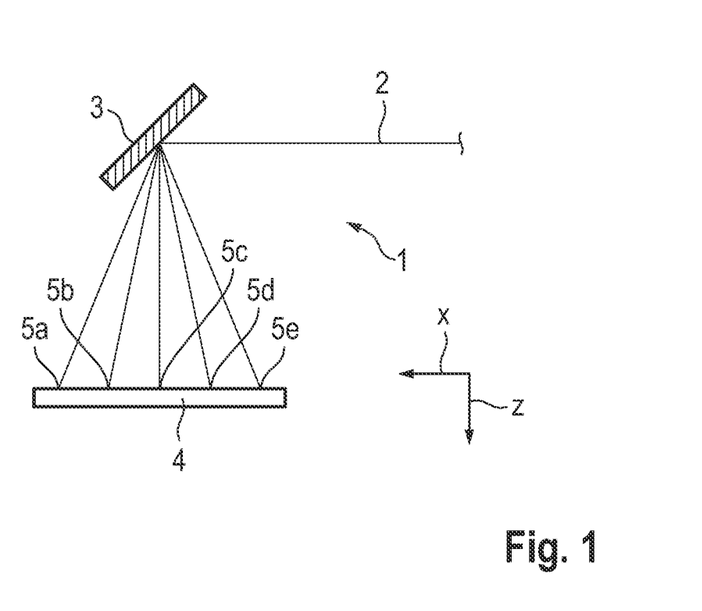
FIG. 1 shows a cross section of a portion of an exemplary optical coherence tomography device.

Conventionally, the B-scan is carried out by virtue of the beam 2 being reflected at a pivotable mirror 3; see FIG. 1. In the B-scan, this leads to the various beams 2 which are incident on a sample 4 at different points of incidence not running parallel to one another. This leads to an inaccuracy in the OCT cross-sectional image 20. For example, if the sample 4 is straight, as depicted in FIG. 1, then the sample 4 appears slightly curved in the OCT cross-sectional image 20. Within the scope of optical coherence tomography, the path traveled through the eye by the beam moreover depends on the properties of the eye. To obtain an OCT cross-sectional image of the eye that is as accurate as possible, the OCT cross-sectional image would have to be corrected in respect of these properties. These properties include the curvature of the cornea of the eye, the composition of the fluid in the anterior eye chamber of the eye, a pressure in the anterior eye chamber, and a shape of the eye and, in particular, of the anterior eye chamber. These properties may change as a result of the cataract treatment because the incision in the cornea may lead to the cornea changing its shape, because the fluid naturally accommodated within the eye is at least partially replaced by artificial fluids such as a physiological buffered saline solution and/or an ophthalmic viscoelastic device during the cataract treatment, and/or because the crystalline lens is removed. Therefore, these properties are at least partially unknown. The OCT cross-sectional image cannot be optimally corrected because these properties are unknown, and so the properties of the intraocular lens cannot be determined in optimal fashion. This may lead to imaging aberrations of the intraocular lens on the retina.

It is therefore the object of the invention to develop a treatment apparatus having an optical coherence tomography device and a method for generating an OCT cross-sectional image, by means of which the OCT cross-sectional image can be generated very accurately.

The treatment apparatus according to the invention for a cataract treatment of an eye comprises a modular intraocular lens, an optical coherence tomography device, and an evaluation unit. The modular intraocular lens comprises a first part having a haptic and a marking, visible in optical coherence tomography, with known dimensions of said marking and a second part having an optics body. Moreover, the modular intraocular lens has a convergence state, in which the second part is in contact with the first part, and a spaced-apart state, in which the second part is spaced apart from the first part. The optical coherence tomography device is configured to record, by means of optical coherence tomography, an OCT cross-sectional image which shows the first part arranged in a capsular bag of the eye and which shows dimensions of the marking in the OCT cross-sectional image. The evaluation unit is configured to create a corrected OCT cross-sectional image by transforming coordinates of the OCT cross-sectional image in such a way that dimensions of the marking in the corrected OCT cross-sectional image are closer to the known dimensions of the marking than the dimensions of the marking in the OCT cross-sectional image.

The method according to the invention for correcting an OCT cross-sectional image showing a first part of a modular intraocular lens, the latter comprising a second part, wherein the first part has a haptic and a marking, visible in optical coherence tomography, with known dimensions of said marking, wherein the second part has an optics body, and wherein the modular intraocular lens has a convergence state, in which the second part is in contact with the first part, and a spaced-apart state, in which the second part is spaced apart from the first part, includes the following step:

performing a coordinate transformation on the OCT cross-sectional image, whereby a corrected OCT cross-sectional image is formed in such a way that dimensions of the marking in the corrected OCT cross-sectional image are closer to the known dimensions of the marking than dimensions of the marking in the OCT cross-sectional image.

In the case of the treatment apparatus and the method, there advantageously is no need to know properties of the eye which during optical coherence tomography influence the path taken through the eye by a beam of electromagnetic radiation. By virtue of the marking with the known dimensions being arranged in the eye, it is possible to correct the OCT cross-sectional image in such a way by means of the coordinate transformation that distances in the corrected OCT cross-sectional image are very accurate. The fact that the beams incident on the eye at different points of incidence are not arranged parallel to one another can also be corrected in the process. Since the distances in the corrected cross-sectional image are very accurate, it is possible to optimally choose the properties of the optics body.

In the case of the treatment apparatus and/or the method, it is preferable for the OCT cross-sectional image not to show the second part. The OCT cross-sectional image particularly preferably shows the first part in the spaced-apart state of the modular intraocular lens.

In the case of the treatment apparatus and/or the method, it is preferable for the coordinate transformation to be a projective transformation. By way of example, the projective transformation can be carried out by $$\begin{bmatrix} h_{11} & h_{12} & h_{13} \\ h_{21} & h_{22} & h_{23} \\ h_{31} & h_{32} & h_{33} \end{bmatrix} * \begin{bmatrix} x \\ z \\ 1 \end{bmatrix} = \begin{bmatrix} x' \\ z' \\ 1 \end{bmatrix}$$

where x and z are the coordinates in the OCT cross-sectional image, x' and z' are the coordinates in the corrected OCT cross-sectional image, and $h_{ab}$ are coefficients. The evaluation unit can be configured to determine the coefficients $h_{ab}$ by virtue of the known dimensions of the marking being represented by reference points in a reference cross-sectional image and the coefficients $h_{ab}$ being chosen such that the pixels associated with the reference points correspond to the reference points in the corrected OCT cross-sectional image. If there is a total of four reference points, it is possible to uniquely determine the coefficients. If there are more than four reference points, then the coefficients $h_{ab}$ can be varied until, in the corrected OCT cross-sectional image, the pixels associated with the reference points come close to the reference points. By way of example, the sum of the squares of the distances from the reference points to the associated pixels can be minimized to this end.

Alternatively, it is preferable for the coordinate transformation to be a polynomial transformation implemented by way of the equations $$x' = \sum_{i=0}^{n} \sum_{j=0}^{n} P_{i,j} x^i z^j$$

and $$z' = \sum_{i=0}^{n} \sum_{j=0}^{n} Q_{i,j} x^i z^j$$

where x and z are the coordinates in the OCT cross-sectional image, x' and z' are the coordinates in the corrected OCT cross-sectional image, and $P_{i,j}$ and $Q_{i,j}$ are coefficients. To determine the coefficients $P_{i,j}$ and $Q_{i,j}$, the number of reference points should be at least $(n+1)^2$. By way of example, n can be at least one. Particularly preferably, n is two, three, or four. By way of example, it is possible to uniquely determine the coefficients $P_{i,j}$ and $Q_{i,j}$ in the case where n=3 and there are 16 reference points. By contrast, if there are more than 16 reference points, then the coefficients $P_{i,j}$ and $Q_{i,j}$ can be approximated. In this case, it is particularly preferable for the evaluation unit to be configured to determine the coefficients $P_{i,j}$ and $Q_{i,j}$ by virtue of the known dimensions of the marking being represented by reference points in a reference cross-sectional image and the coefficients $P_{i,j}$ and $Q_{i,j}$ being varied until, in the corrected OCT cross-sectional image, the pixels associated with the reference points come close to the reference points. By way of example, the sum of the squares of the distances from the reference points to the associated pixels can be minimized to this end.

It is preferable for the evaluation unit to be configured to determine at least one geometric parameter of the eye from the corrected OCT cross-sectional image, the at least one geometric parameter being selected from the following group: an extent of the anterior eye chamber of the eye, in particular in the direction of the optical axis of the eye, a distance from the cornea of the eye to the first part, in particular in the direction of the optical axis of the eye, a curvature of an exterior corneal side of the eye, and a curvature of an interior corneal side of the eye.

The evaluation unit is preferably configured to calculate a refractive power of the optics body by means of the at least one geometric parameter. A number of known methods and/or formulas are available to this end. Exemplary formulas are: Holladay I, Holladay II, Haigis, ZCALC and Olcen C.

The marking may be formed by a known shape of the first part. Preferably, the marking is formed at least in part by protrusions, recesses, and/or crystalline particles. The crystalline particles are visible in the OCT cross-sectional image with a particularly high contrast.

It is preferable for the first part to have a ring portion which in its interior delimits a ring cutout, the latter being configured to accommodate the optics body and hence bring the modular intraocular lens from the spaced-apart state into the convergence state, with the marking being formed at least in part by the ring portion.

The method preferably includes the following step: —determining at least one geometric parameter of the eye from the corrected OCT cross-sectional image, the at least one geometric parameter being selected from the following group: an extent of the anterior eye chamber of the eye, in particular in the direction of the optical axis of the eye, a distance from the cornea of the eye to the first part, in particular in the direction of the optical axis of the eye, a curvature of an exterior corneal side of the eye, and a curvature of an interior corneal side of the eye.

Preferably, the method includes the following step: —calculating a refractive power of the optics body by means of the at least one geometric parameter.

Recording the OCT cross-sectional image is preferably not a part of the method.

The invention is explained in detail in the hereinbelow with reference to the appended schematic drawings, in which.

Figure 4:
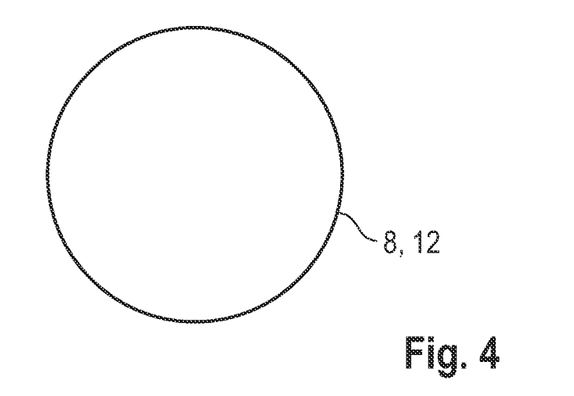
FIG. 4 shows a plan view of an example of a second part of the modular intraocular lens.
Figure 5:
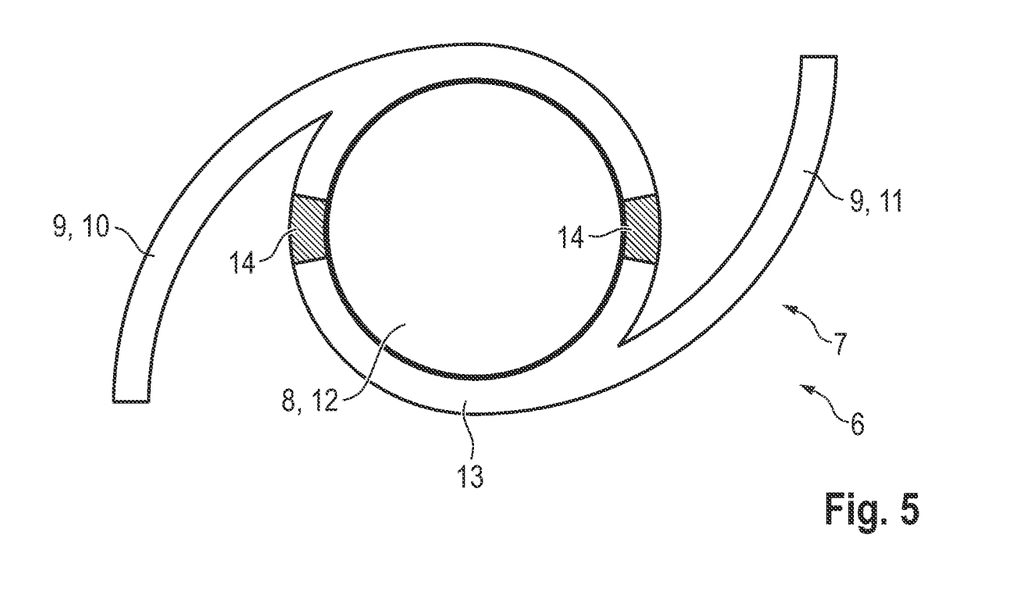
FIG. 5 shows a plan view of the modular intraocular lens with the first part from FIG. 2 and the second part from FIG. 4.
Figure 7:
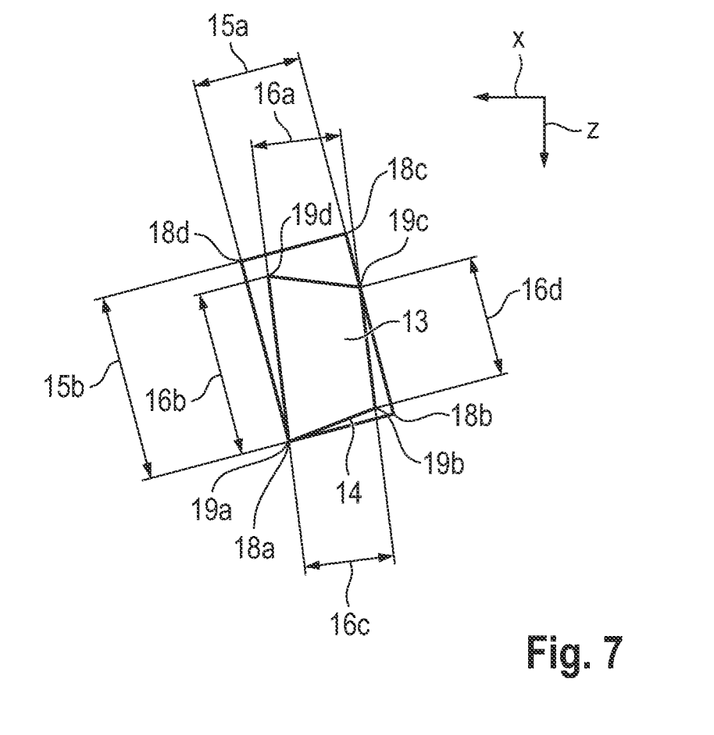
FIG. 7 shows a schematic drawing for illustrating an image correction.
Figure 8:
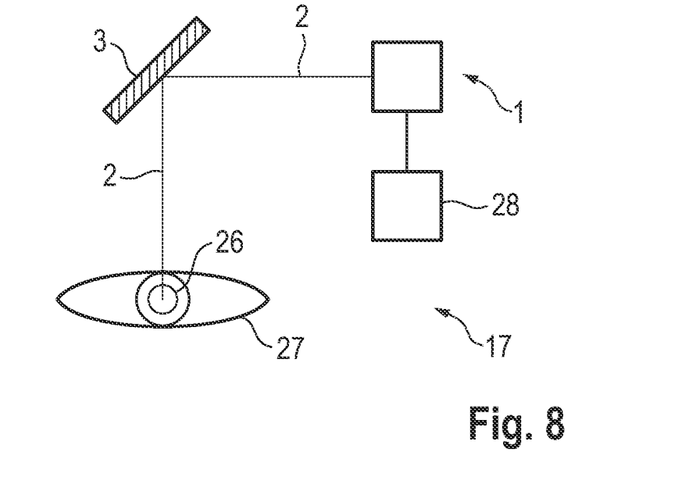
FIG. 8 shows a schematically illustrated treatment apparatus according to the invention.

FIG. 8 shows a treatment apparatus 17 for a cataract treatment of an eye 27, the treatment apparatus 17 comprising a modular intraocular lens 6 (see FIG. 5), an optical coherence tomography device 1, and an evaluation unit 28. The modular intraocular lens 6 comprises a first part 7 (see FIGS. 2 and 3) having a haptic 9 and a marking 14, visible in optical coherence tomography, with known dimensions 15a, 15b of said marking 14 and a second part 8 having an optics body 12 (see FIG. 4). The modular intraocular lens 6 has a convergence state, in which the second part 8 is in contact with the first part 7, and a spaced-apart state, in which the second part 8 is spaced apart from the first part 7. The optical coherence tomography device 1 is configured to record, by means of optical coherence tomography, an OCT cross-sectional image 20 (see FIG. 6) which shows the first part 7 arranged in a capsular bag of the eye 27 and which shows dimensions 16a to 16d of the marking 14 in the OCT cross-sectional image 20 (see FIG. 7). The evaluation unit 28 is configured to create a corrected OCT cross-sectional image by transforming coordinates of the OCT cross-sectional image 20 in such a way that dimensions of the marking 14 in the corrected OCT cross-sectional image are closer to the known dimensions 15a, 15b of the marking 14 than the dimensions 16a to 16d of the marking 14 in the OCT cross-sectional image 20. By way of example, the evaluation unit 28 can comprise a processor. In particular, the evaluation unit 28 can be formed by a computer.

FIG. 1 illustrates how the OCT cross-sectional image 20 (see FIG. 6) can be obtained. The optical coherence tomography device 1 generates a beam 2 of electromagnetic radiation, more particularly infrared radiation, with the beam 2 being formed by a measurement arm of a Michelson interferometer. The beam 2 is deflected at a pivotable mirror 3 and guided to a sample 4, which is to say the eye 27. The beam 2 can be displaced in an x-direction (this is also referred to as a B-scan) by virtue of the mirror 3 being pivoted and hence can be guided to different points of incidence 5a to 5e on the eye 27, which in particular are all located in the same plane. Optical coherence tomography provides information regarding the depth along the path of the beam 2 in the eye 27 (to this end, a mirror in a reference arm of the Michelson interferometer is longitudinally displaced), oriented in a z-direction in FIG. 1, at which reflecting or scattering structures are arranged. As a result, the OCT cross-sectional image 20 can be obtained by the B-scan, with the x-direction and the z-direction likewise being plotted in FIG. 6. Each of the points of incidence 5a to 5e corresponds to a respective column in the OCT cross-sectional image 20 in FIG. 6.

Figure 2:
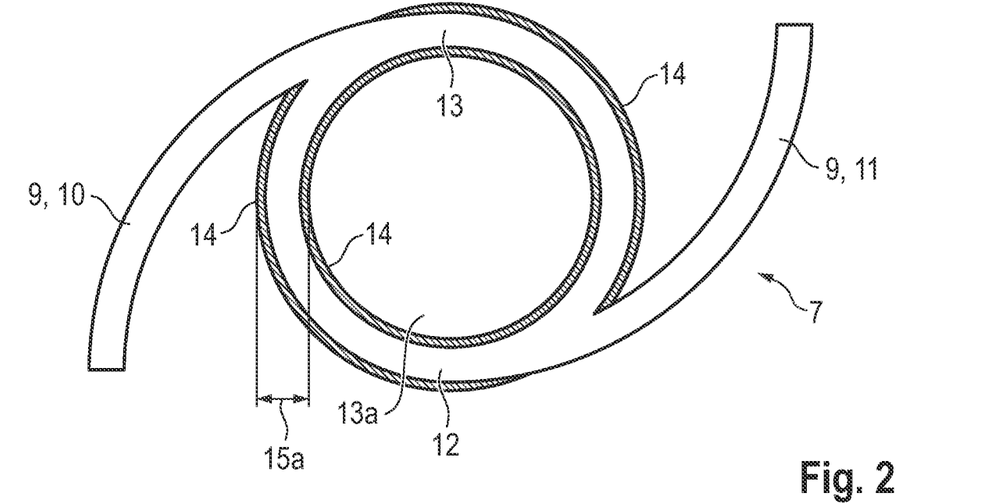
FIG. 2 shows a plan view of a first example of a first part of a modular intraocular lens.
Figure 3:
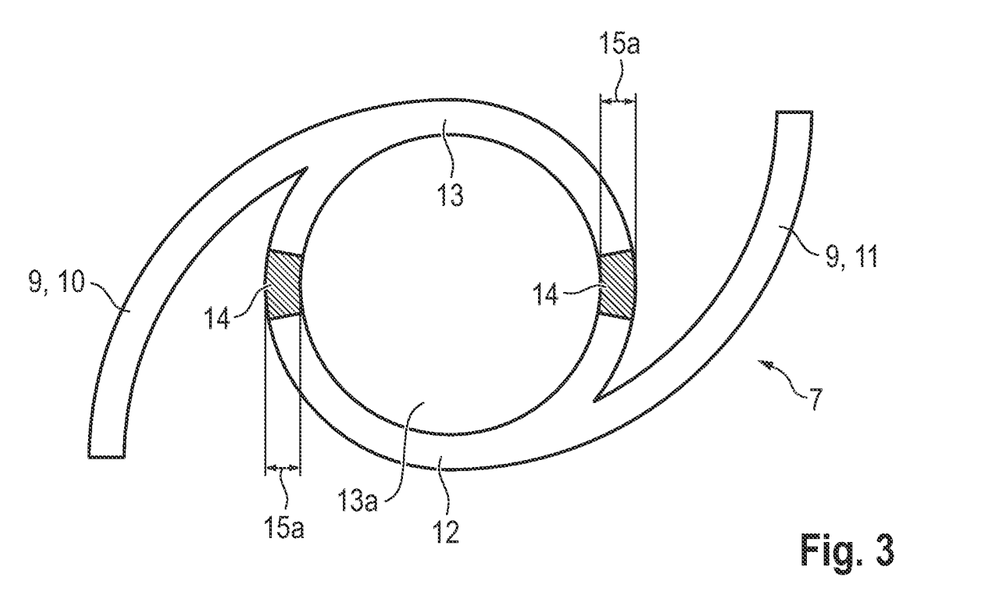
FIG. 3 shows a plan view of a second example of the first part.

The marking 14 can be formed by any shape of the first part 7 that is visible with a sufficiently high contrast in the OCT cross-sectional image 20. FIGS. 2 and 3 show examples of the marking 14. The first part 7 can comprise a ring portion 13 which in its interior delimits a ring cutout 13a, the latter being configured to accommodate the optics body 12. By way of example, the modular intraocular lens 6 can be brought from the spaced-apart state into the convergence state by accommodating the optics body 12 in the ring cutout 13a. The haptic 9 may comprise a first haptic arm 10 and a second haptic arm 11, which are each fastened to the ring portion 13. The marking 14 may be formed by the ring portion 13 at least in part. By way of example, the known dimension 15a of the marking 14 may include a width of the ring portion 13. As an alternative or in addition, it is conceivable for the known dimension to include a height 15b of the ring portion 13 (cf. FIG. 7). It is also conceivable that the marking 14 is formed at least in part by protrusions and/or recesses; see FIG. 3 (the marking 14 depicted there may be both a protrusion and a recess). The known dimension 15a of the marking 14 may include a width of the protrusion and/or recess. As an alternative or in addition, it is conceivable for the known dimension to include a height 15b of the protrusion and/or recess (not depicted in FIG. 3). It is also conceivable that the first part 7 comprises crystalline particles which form the marking 14. It is conceivable that the first part 7 comprises a further optics body.

FIG. 7 illustrates how parameters for carrying out the coordinate transformation can be determined. The marking according to FIG. 7 can be a cross section of the ring portion 13, for example. The evaluation unit 28 can be configured to determine the parameters by virtue of the known dimensions 15a, 15b of the marking 14 being represented by reference points 18a to 18d in a reference cross-sectional image. For each reference point 18a to 18d, there is an associated pixel 19a to 19d in the corrected OCT cross-sectional image. In the example of FIG. 7, the pixel 19a belongs to the reference point 18a, the pixel 19b belongs to the reference point 18b, the pixel 19c belongs to the reference point 18c, and the pixel 19d belongs to the reference point 18d. The evaluation unit 28 can be configured to vary the parameters until, in the corrected OCT cross-sectional image, the pixels 19a to 19d associated with the reference points 18a to 18d come close to the reference points 18a to 18d. In FIG. 7, this leads to the pixel 19a being brought closer to the reference point 18a, the pixel 19b being brought closer to the reference point 18b, the pixel 19c being brought closer to the reference point 18c, and the pixel 19d being brought closer to the reference point 18d.

By way of example, the coordinate transformation can be a projective transformation. By way of example, this can be implemented by a matrix multiplication of the following form:

$$\begin{bmatrix} h_{11} & h_{12} & h_{13} \\ h_{21} & h_{22} & h_{23} \\ h_{31} & h_{32} & h_{33} \end{bmatrix} * \begin{bmatrix} x \\ z \\ 1 \end{bmatrix} = \begin{bmatrix} x' \\ z' \\ 1 \end{bmatrix}.$$

The parameters consequently are the coefficients $h_{ab}$. x and z are the coordinates in the OCT cross-sectional image 20. x' and z' are the coordinates in the corrected OCT cross-sectional image.

Alternatively, the coordinate transformation can be a polynomial transformation implemented by way of the equations $$x' = \sum_{i=0}^{n}\sum_{j=0}^{n} P_{i,j} x^i z^j$$

and $$z' = \sum_{i=0}^{n}\sum_{j=0}^{n} Q_{i,j} x^i z^j$$

where x and z are the coordinates in the OCT cross-sectional image, x' and z' are the coordinates in the corrected OCT cross-sectional image, and $P_{i,j}$ and $Q_{i,j}$ are coefficients. The parameters are the coefficients $P_{i,j}$ and $Q_{i,j}$.

After the parameters have been determined, the coordinate transformation can also be applied to further points and, in particular, to all remaining points in the OCT cross-sectional image 20 in order to obtain the corrected OCT cross-sectional image.

FIG. 6 shows an exemplary OCT cross-sectional image 20 of the eye 27. A cornea 21 of the eye 27, an anterior eye chamber 24 of the eye 27, an iris 25 of the eye 27, and a pupil 26 of the eye 27 are identifiable in the OCT cross-sectional image 20. The OCT cross-sectional image 20 also shows the first part 7 of the modular intraocular lens 6. Following the correction according to the invention of the OCT cross-sectional image 20, distances and other geometric parameters can be read with greater accuracy from the corrected OCT cross-sectional image than from the OCT cross-sectional image 20. By way of example, the geometric parameters may be selected from the following group: a curvature of an exterior corneal side 22, a curvature of an interior corneal side 23, an extent of the anterior eye chamber of the eye, in particular in the direction of the optical axis of the eye 27, a distance from the cornea 21 of the eye 27 to the first part 7, in particular in the direction of the optical axis of the eye 27. The direction of the optical axis of the eye 27 may coincide with the z-direction.

LIST OF REFERENCE SIGNS

1 Optical coherence tomography device
2 Beam
3 Mirror
4 Sample
5a Point of incidence
5b Point of incidence
5c Point of incidence
5d Point of incidence
5e Point of incidence
6 Modular intraocular lens
7 First part
8 Second part
9 Haptic
10 First haptic arm
11 Second haptic arm
12 Optics body
13 Ring portion
13a Cutout
14 Marking
15a Known dimension of the marking
15b Known dimension of the marking
16a Dimension of the marking in the OCT cross-sectional image
16b Dimension of the marking in the OCT cross-sectional image
16c Dimension of the marking in the OCT cross-sectional image
16d Dimension of the marking in the OCT cross-sectional image
17 Treatment apparatus
18a Reference point
18b Reference point
18c Reference point
18d Reference point
19a Pixel
19b Pixel
19c Pixel
19d Pixel
20 OCT cross-sectional image
21 Cornea
22 Exterior corneal side
23 Interior corneal side
24 Anterior eye chamber
25 Iris
26 Pupil
27 Eye
28 Evaluation unit
x Coordinate
z Coordinate

The invention claimed is:

1. A treatment apparatus for a cataract treatment of an eye, having a modular intraocular lens, which comprises a first part having a haptic and a marking, visible in optical coherence tomography, with known dimensions of said marking and a second part having an optics body and which has a convergence state, in which the second part is in contact with the first part, and a spaced-apart state, in which the second part is spaced apart from the first part, having an optical coherence tomography device, which is configured to record, by means of optical coherence tomography, an OCT cross-sectional image which shows the first part arranged in a capsular bag of the eye and which shows dimensions of the marking in the OCT cross-sectional image, and having an evaluation unit which is configured to create a corrected OCT cross-sectional image by transforming coordinates of the OCT cross-sectional image in such a way that dimensions of the marking in the corrected OCT cross-sectional image are closer to the known dimensions of the marking than the dimensions of the marking in the OCT cross-sectional image.

2. The treatment apparatus as claimed in claim 1, wherein the coordinate transformation is a projective transformation.

3. The treatment apparatus as claimed in claim 1, wherein the coordinate transformation is a polynomial transformation implemented by way of the equations $$x' = \sum_{i=0}^{n}\sum_{j=0}^{n} P_{i,j} x^i z^j$$

and $$z' = \sum_{i=0}^{n}\sum_{j=0}^{n} Q_{i,j} x^i z^j$$

where x and z are the coordinates in the OCT cross-sectional image, x' and z' are the coordinates in the corrected OCT cross-sectional image, and $P_{i,j}$ and $Q_{i,j}$ are coefficients.

4. The treatment apparatus as claimed in claim 3, wherein the evaluation unit is configured to determine the coefficients $P_{i,j}$ and $Q_{i,j}$ by virtue of the known dimensions of the marking being represented by reference points in a reference cross-sectional image and the coefficients $P_{i,j}$ and $Q_{i,j}$ being varied until, in the corrected OCT cross-sectional image, the pixels associated with the reference points come close to the reference points.

5. The treatment apparatus as claimed in claim 1, wherein the evaluation unit is configured to determine at least one property of the eye from the corrected OCT cross-sectional image, the at least one property being selected from the following group: an extent of the anterior eye chamber of the eye, in particular in the direction of the optical axis of the eye, a distance from the cornea of the eye to the first part, in particular in the direction of the optical axis of the eye, a curvature of an exterior corneal side of the eye, and a curvature of an interior corneal side of the eye.

6. The treatment apparatus as claimed in claim 5, wherein the evaluation unit is configured to calculate a refractive power of the optics body by means of the at least one property.

7. The treatment apparatus as claimed in claim 1, wherein the marking is formed at least in part by protrusions, recesses, and/or crystalline particles.

8. The treatment apparatus as claimed in claim 1, wherein the first part has a ring portion which in its interior delimits a ring cutout, the latter being configured to accommodate the optics body, with the marking being formed at least in part by the ring portion.

9. A method for correcting an OCT cross-sectional image showing a first part of a modular intraocular lens, the latter comprising a second part, wherein the first part has a haptic and a marking, visible in optical coherence tomography, with known dimensions of said marking, wherein the second part has an optics body, wherein the modular intraocular lens has a convergence state, in which the second part is in contact with the first part, and a spaced-apart state, in which the second part is spaced apart from the first part, and wherein the method includes the following step:

performing a coordinate transformation on the OCT cross-sectional image, whereby a corrected OCT cross-sectional image is formed in such a way that dimensions of the marking in the corrected OCT cross-sectional image are closer to the known dimensions of the marking than dimensions of the marking in the OCT cross-sectional image.

10. The method as claimed in claim 9, wherein the OCT cross-sectional image does not show the second part.

* * * * *